United States Patent
Ikemoto

(10) Patent No.: US 12,133,929 B2
(45) Date of Patent: Nov. 5, 2024

(54) ANTIMICROBIAL AGENT CONTAINING HYPOCHLOROUS ACID

(71) Applicant: FREEKIRA PHARMACEUTICAL INC., Tokyo (JP)

(72) Inventor: Yoshikatsu Ikemoto, Tokyo (JP)

(73) Assignee: FREEKIRA PHARMACEUTICAL INC., Tokyo (JP)

(*) Notice: Subject to any disclaimer, the term of this patent is extended or adjusted under 35 U.S.C. 154(b) by 668 days.

(21) Appl. No.: 16/768,229

(22) PCT Filed: Nov. 29, 2018

(86) PCT No.: PCT/JP2018/044071
§ 371 (c)(1),
(2) Date: Aug. 5, 2020

(87) PCT Pub. No.: WO2019/107510
PCT Pub. Date: Jun. 6, 2019

(65) Prior Publication Data
US 2020/0390919 A1 Dec. 17, 2020

(30) Foreign Application Priority Data

Nov. 29, 2017 (JP) .................................. 2017-228845
Nov. 5, 2018 (JP) .................................. 2018-207983

(51) Int. Cl.
*A61L 2/18* (2006.01)
*A61L 101/06* (2006.01)

(52) U.S. Cl.
CPC ............. *A61L 2/18* (2013.01); *A61L 2101/06* (2020.08); *A61L 2202/24* (2013.01)

(58) Field of Classification Search
CPC ....................................................... A61L 2/18
See application file for complete search history.

(56) References Cited

U.S. PATENT DOCUMENTS

2003/0138498 A1 7/2003 Yoshikawa et al.
2003/0155549 A1 8/2003 Yoshikawa et al.
(Continued)

FOREIGN PATENT DOCUMENTS

CN 1433269 A 7/2003
EP 1236398 A1 9/2002
(Continued)

OTHER PUBLICATIONS

Rutala, William A., et al., Guideline for Disinfection and Sterilization in Healthcare Facilities, 2008, 2008, Center for Disease Control, pp. 23, 34 (Year: 2008).*
(Continued)

*Primary Examiner* — Donald R Spamer
*Assistant Examiner* — Priscilla Browning
(74) *Attorney, Agent, or Firm* — Locke Lord LLP

(57) ABSTRACT

The purpose of the present invention is to provide a hypochlorous acid aqueous solution having excellent antimicrobial effect and safety. An antimicrobial agent is provided, which is a hypochlorous acid aqueous solution with a pH 6.0 to 6.7, wherein the effective chlorine concentration in the aqueous solution is from 50 to 260 ppm. Further, a sterilization method is provided, which is characterized by immersing the member to undergo sterilization treatment in the aforementioned antimicrobial agent for 0.5 to 10 minutes. The antimicrobial agent has a broad antimicrobial spectrum of norovirus, *Staphylococcus aureus* and other bacteria, yeast belonging to *Rhodotorula*, and *Cladosporium cladospolioides* and other fungi.

19 Claims, 5 Drawing Sheets

(56) References Cited

U.S. PATENT DOCUMENTS

| | | | | |
|---|---|---|---|---|
| 2004/0232381 | A1* | 11/2004 | Pinza | C01B 11/062 |
| | | | | 252/187.26 |
| 2007/0231247 | A1* | 10/2007 | Bromberg | A61P 17/00 |
| | | | | 423/473 |
| 2008/0003171 | A1* | 1/2008 | Smith | B09B 3/0075 |
| | | | | 422/184.1 |
| 2008/0008621 | A1* | 1/2008 | Ikeda | A61L 2/18 |
| | | | | 510/161 |
| 2008/0067078 | A1* | 3/2008 | Kitaori | A61L 2/0088 |
| | | | | 204/252 |
| 2010/0285151 | A1* | 11/2010 | Goldan | A61P 31/04 |
| | | | | 424/662 |
| 2012/0269904 | A1 | 10/2012 | Northey | |
| 2014/0328945 | A1* | 11/2014 | Adams | A23L 3/358 |
| | | | | 424/661 |
| 2015/0010604 | A1* | 1/2015 | Ishii | A01N 65/08 |
| | | | | 424/405 |
| 2015/0196590 | A1 | 7/2015 | Sampson et al. | |
| 2016/0339132 | A1* | 11/2016 | Cosman | F26B 9/003 |
| 2017/0208812 | A1* | 7/2017 | Som | A61L 2/18 |
| 2018/0199576 | A1 | 7/2018 | Kemoto | |
| 2019/0151356 | A1 | 5/2019 | Goldan et al. | |

FOREIGN PATENT DOCUMENTS

| | | | |
|---|---|---|---|
| JP | 2001-311095 | A | 11/2001 |
| JP | 2002-502372 | A | 1/2002 |
| JP | 2003-034605 | A | 2/2003 |
| JP | 4740892 | B2 | 8/2011 |
| JP | 5307351 | B2 | 10/2013 |
| JP | 2015-104719 | A | 6/2015 |
| WO | 1998/052410 | A2 | 11/1998 |
| WO | 2008/089268 | A2 | 7/2008 |
| WO | 2010/148004 | A1 | 12/2010 |
| WO | 2014/115860 | A1 | 7/2014 |
| WO | WO-2016170818 | A1 * | 10/2016 |
| WO | WO-2017002277 | A1 * | 1/2017 ............ A01N 25/08 |
| WO | 2017/047169 | A1 | 3/2017 |

OTHER PUBLICATIONS

Mady A. Ismail, "Inhibitory Effects of Na-Hypochlorite and Heating on the Mycobiota Associated with Fruits or Juice of Passion (*Passiflora edulis* Sims) in Uganda", Mycobiology, vol. 34 (2), 2006, pp. 92-98. (cited in the Jan. 5, 2022 Search Report issued for EP18884625.7).

Supplementary European Search Report mailed Jan. 5, 2022, issued for European Patent Application No. 18884625.7.

Ota Yoshinori, "Sterilization of microbes by using disinfection water consist primarily of hypochlorous acid as a main ingredient," Clinical Microbiology, 2006, vol. 33, No. 3, p. 275-279. (cited in the ISR).

International Preliminary Report on Patentability created Feb. 25, 2020, issued for PCT/JP2018/044071.

International Search Report mailed Mar. 5, 2019, issued for PCT/JP2018/044071.

"Regulation (EU) No. 528/2012 concerning the making available on the market and use of biocidal products Evaluation of active substances: Active chlorine released from sodium hypochlorite", Jan. 1, 2017, pp. 1-112. (cited in the Jan. 13, 2023 Office Action issued for EP18884625.7).

Office Action dated Jan. 13, 2023, issued for European Patent Application No. 18884625.7.

"Regulation (EU) No. 528/2012 concerning the making available on the market and use of biocidal products, Evaluation of active substances, Assessment Report", Bacillus thuringiensis subsp. Kurstaki, Serotype 3a 3b, Strain ABTS-351, Feb. 2016, pp. 1-96. (cited in the Sep. 27, 2023 Office Action issued for EP18 884 625.7).

Office Action dated Sep. 27, 2023, issued for EP18 884 625.7.

* cited by examiner

Fig. 2

<Clostridium butyricum NBRC13949>

CFU/mL

- ——— pH6.5
- -------- pH5.5
- — — pH4.0
- – – – pH3.0

$1 \times 10^6$, $1 \times 10^5$, $1 \times 10^4$, $1 \times 10^3$, $1 \times 10^2$ 0, 10sec, 1min, 5min, 10min → Treatment time

[Measuring limit : $1 \times 10^2$]

Fig. 3

CFU/mL

<Clostridium sporogenes IFO13950>

- ——— : pH6.5
- -------- : pH5.5
- — — : pH4.0
- – – – : pH3.0

$1 \times 10^8$, $1 \times 10^7$, $1 \times 10^6$, $1 \times 10^5$, $1 \times 10^4$, $1 \times 10^3$, $1 \times 10^2$ 0, 10sec, 1min, 5min, 10min → Treatment time

[Measuring limit : $1 \times 10^2$]

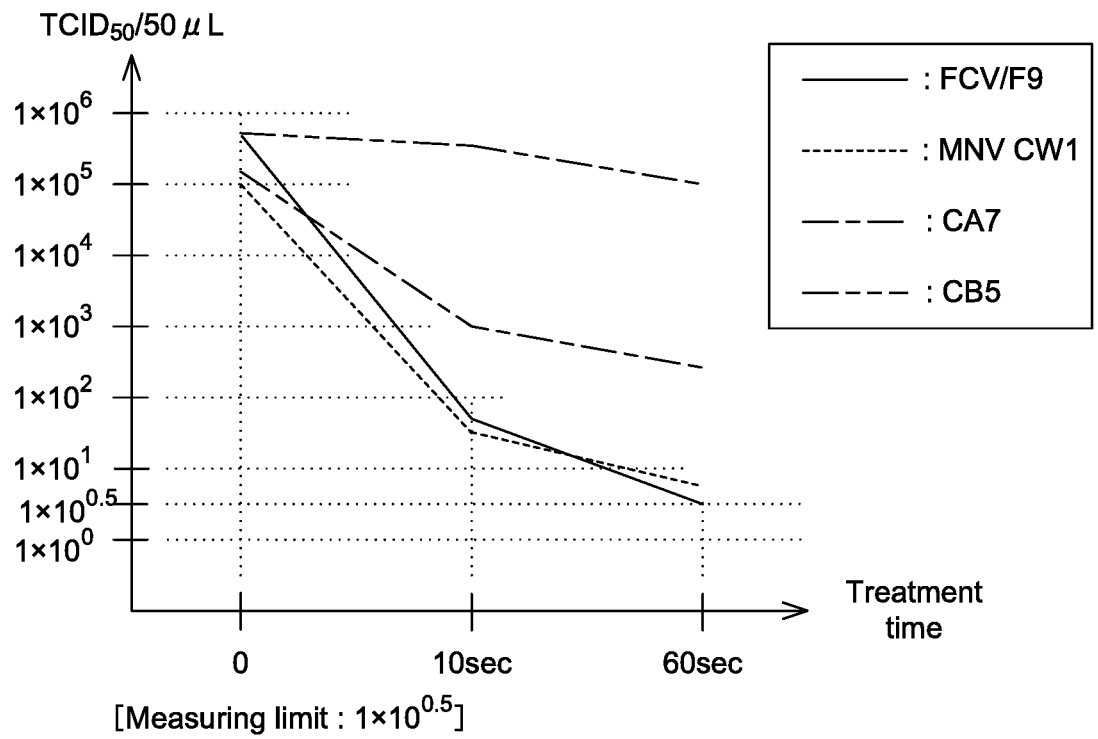
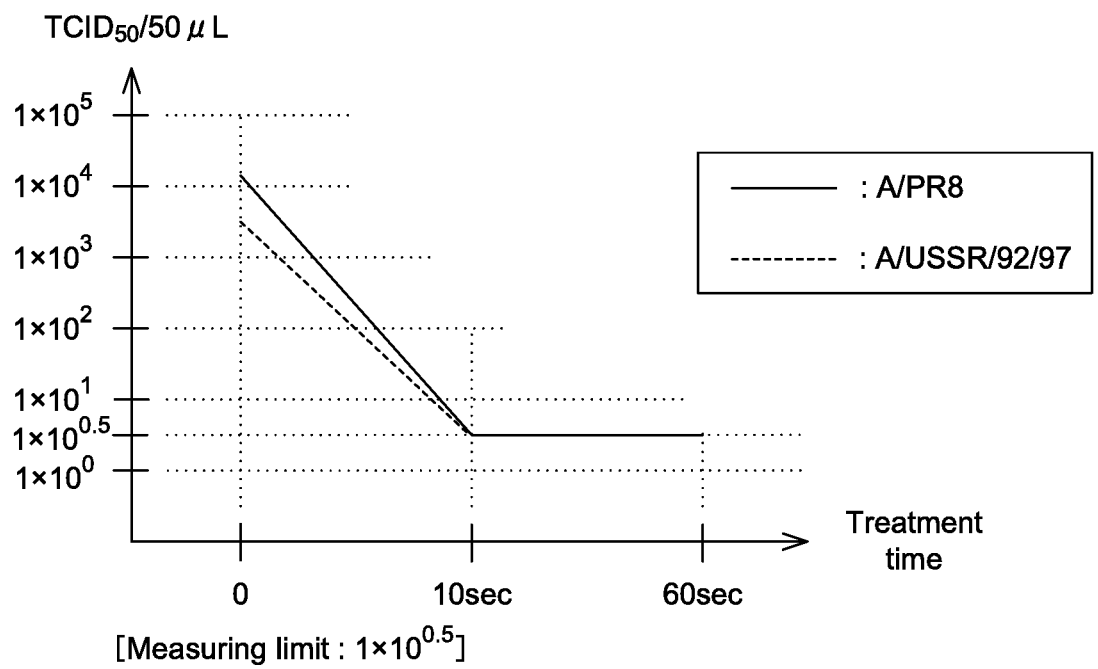

ANTIMICROBIAL AGENT CONTAINING HYPOCHLOROUS ACID

TECHNICAL FIELD

The present invention relates to an antimicrobial agent comprising hypochlorous acid aqueous solution, aqueous hypochlorous acid solution, having both excellent bactericidal and safety.

BACKGROUND OF INVENTION

Recently, small sized medical devices such as an endoscope and the like, which provides minimally-invasive excision of an affected area, became widely used. The treatment by using the small-sized medical devices have several advantages such as less physical burden for a patient, shortened hospitalization and the like compared to a surgical operation with highly-advanced invasion, for example, thoracotomy, abdominal operation, and the like. On the other hand, these devices are highly contaminated by adhesion of blood, bacteria and the like. Therefore, insufficient sterilization will expand infection.

Disinfection of the devices required advanced antimicrobial agent, and at present, glutaral or phtharal, both including formalin, and peracetic acid are used.

Conventionally, hypochlorous acid is used for disinfection of hands and fingers, that of tap water, that of foods and the like as a form of hypochlorite. For example, it is known that a kind of hypochlorite, sodium hypochlorite (sodium hypochlorite: NaClO) has oxidation activity, bleaching activity, and bactericidal activity; and degerming agents include hypochlorite is commercially available in the form of aqueous solution or powder. Effective chlorine contents contained in such commercially available products are generally about 5%, 6%, 10% and 12%.

Sodium hypochlorite is sodium salt of hypochlorous acid, and it has oxidation activity, bleaching activity, and bactericidal activity. It is comparatively stable in an alkaline area, however, is dangerous in acidic area, because it is quite rapidly decomposed to generate chlorine gas. Concretely, under pH 7 or lower pH, the decomposition reaction occurs, and pH 5 or lower pH, it generates chlorine gas rapidly. Therefore, it is produced as strong alkaline solution not less than pH 12. In order to prevent such danger, an apparatus for preventing chlorine gas generation (see, patents document 1 and 2).

PRIOR ART

Patent Documents

Patent document 1 JP 4740892 B
Patent document 2 JP 5307351 B

SUMMARY OF THE INVENTION

Problems to be Solved by the Invention

At present, 3 agents are mainly used as advanced antimicrobial agents. However, it is known that even if peracetic acid, the most effective one, is used, it takes 10 minutes for sterilization, and it deteriorates the material used in the medical devices.

Both of glutaral and phtharal hardly deteriorates them, however it takes long time for the sterilization, 6 hours by glutaral, and 96 hours by phtharal. Also, glutaral has a disadvantage that has strong irritating odor. Furthermore, phtharal binds protein tightly so that it makes rinse difficult, if dirt remains.

In order to proceed with treatment effectively, a microbicidal agent has following properties: which terminates sterilization in short time; which does not deteriorate the material; and which does not bind the proteins tightly. Therefore, there is strong social need for the microbicidal agent which makes short time sterilization without deterioration the material and tight binding to the proteins.

Also, it is known that an injectable having low pH gives strong pain. Also, hypochlorous acid solution having strong alkaline property contacts human skin (pH about 4.5 to 6) sometimes gives strong pain, when it is used for sterilization of the medical devices. Therefore, there is higher needs for the microbicidal agent having pH in neutral range.

Furthermore, the pharmaceutical agent used as the microbicidal agent is required both to have a high bactericidal activity and to secure high safety. Therefore, there is strong social needs for the disinfectant having these two properties.

Also, it is desirable for the microbicidal agent to give affection against not only the bacteria, but also viruses or fungi (molds). Therefore, there is strong social needs for the microbicidal agent having plural effects such as antibacterial, antiviral, and anti-fungal effects.

Means for Solving the Problem

The present invention is completed under such conditions, and its purpose is to provide an antimicrobe agent having both of an excellent microbicidal effects and safety, which is sometimes referred to as a "disinfectant" hereinbelow. Namely, an agent that has a plurality of effects such as bactericidal effect, antiviral effect, antifungal effect and the like is collectively referred to as the "microbicidal agent", which is sometimes referred to as the "disinfectant".

One aspect of the invention is an antimicrobial agent including a hypochlorous acid aqueous solution, wherein effective chlorine concentration in said aqueous solution is from 150 to 260 ppm, and pH range of said aqueous solution is between 3.0 and 6.7, whereby said antimicrobial agent disinfects microbe within 1 minute. Here, the bacterium is any one of bacterium selected from the group consisting of *Clostridium butyricum* and *Clostridium sporogenes*.

Another aspect of the present invention is the antimicrobial agent, wherein the effective chlorine concentration range in said aqueous solution is from 50 to 260 ppm, and pH range of said aqueous solution is between 3.0 and 6.7, for inhibiting the growth of any one of microbe selected from the group consisting of a yeast, a fungus, and a virus. It is preferable that said aqueous solution has the effective chlorine concentration from 50 to 260 ppm, and pH range thereof is between 6.3 and 6.7.

Here, it is the yeast is preferably any one of yeast belonging *Rhodotorula* sp. The fungus is preferably any one of fungus selected from the group consisting of *Cladosporium cladosporioides, Penicillium roqueforti, Penicillium glabrum, Aspergillus niger, Eurotium amstelodami, Neosartorya fischeri, Emericella nidulans, Fusarium*, and *Alternaria*. Also, the antimicrobial agent has an antiviral effect, and the virus is preferably Norovirus.

More another aspect of the present invention is the antimicrobial agent, of which effective chlorine concentration range in said aqueous solution is between 150 and 260 ppm, and pH range of said aqueous solution is between 3.0 and 6.5, whereby said antimicrobial agent disinfects viruses within 10 seconds. Here, the virus is preferably any one of virus selected from the group consisting of Feline panleukopenia virus, Canine parvovirus, and Measles virus.

Note that said hypochlorous acid aqueous solution preferably consists of sodium hypochlorite as a food additive, purified water as defined by the Japanese Pharmacopoeia, and dilute hypochlorous acid solution as defined in the Japanese Pharmacopoeia.

One of another aspect of the present invention is a method for disinfecting a microbe comprising a step; immersing a microbe in the antimicrobial agent for a period from 0.5 minutes to 10 minutes.

One of another aspect of the present invention is a method for disinfecting a microbe comprising a step; immersing any one of microbe selected from the group consisting of the yeast, the fungus, and the virus in the antimicrobial agent for a period from 0.5 minutes to 10 minutes.

One of another aspect of the present invention is a method for disinfecting a microbe comprising a step; immersing the virus in the antimicrobial agent for a period from 10 seconds to 60 seconds.

Advantageous Effect of Invention

According to the present invention, the hypochlorous aqueous solution both having excellent bactericidal effects and safety is prepared, and it is also available for the pharmaceutical agent.

BRIEF EXPLANATIONS OF DRAWINGS

FIG. 2 is the graph showing bactericidal effects against *Clostridium butyricum* NBRC13949.

FIG. 3 is the graph showing bactericidal effects against *Clostridium sporogenes* IFO13950.

FIG. 5 is the graph showing the antiviral effect against measles virus (Measles virus) ATCC VR-24.

FIG. 6 is the graph showing the antiviral effects against Feline panleukopenia virus, Canine parvovirus, and Coxsackie virus.

FIG. 7 is the graph showing the antiviral effect against Influenza virus.

FIG. 8 is the graph showing the antiviral effect against Herpes simplex virus.

FIG. 9 is the graph showing the antiviral effect against Adeno virus.

EMBODIMENT CARRYING OUT INVENTION

Hereinbelow, the aqueous hypochlorous acid solution of one embodiment of the present invention.

(The Aqueous Hypochlorous Acid Solution and the Preparation Thereof)

The antimicrobe agent has an aqueous solution form produced by dissolving sodium hypochlorite into purified water to prepare aqueous solution and then adjusting pH with diluted hydrochloric acid. Here, both of sodium hypochlorite and diluted hydrochloride are approved as food additives, and the purified water is also described in Japan Pharmacopoeia. Therefore, the antimicrobe of the present invention is extremely safe.

Concretely, sodium hypochlorite is dissolved in the purified water so as to be the range from 0.018 to 0.026 w/v %, preferably 0.026 w/v %, to prepare an aqueous sodium hypochlorite solution. The aqueous sodium hypochlorite solution is prepared so as to have pH 6.0 to 6.5 by using dilute hydrochloric acid (about 9.5 to 10.5 w/v %) and then stirred to mix. Hereinbelow, the aqueous solution obtained as described above is referred to as a "aqueous hypochlorous acid solution".

It is preferable that effective chlorine concentration in the aqueous hypochlorous acid solution is in the range from about 50 ppm to about 260 ppm, preferably about 200 ppm to about 210 ppm, depending on species of the microbes, because of securing high microbicidal effect. The solution may be obtained, for example, by using at least 99.9% of purified water and remained less than 0.1% of mixture containing about the same amount of sodium hypochlorite solution with effective chlorine concentration 12% and dilute hydrochloric acid solution with about 10% concentration thereof, when total amount of the solution is 100%.

For example, when the aqueous hypochlorous acid solution which has the effective chlorine concentration in the range from about 200 ppm to about 780 ppm is used as an original, equivalent volume or triple volume of tap water to that of the aqueous hypochlorous acid solution is added thereto. By this, the effective chlorine concentration in the diluted solution becomes ½ or ¼, and the diluted solution may be used as the antimicrobe.

Also, in the aqueous hypochlorous acid solution, both of the effective concentration and pH are adjusted in the range from about 150 ppm to about 260 ppm, and 3.0 to 6.5 for the use as the antimicrobial agent.

Noe that the aqueous hypochlorous acid solution is manually prepared by mixing each raw material in the preparation. However, the aqueous hypochlorous acid solution may be prepared by utilizing a commercially available manufacturing device of the aqueous hypochlorous acid solution (see, Patent documents #1 and #2).

Setting pH of the aqueous hypochlorous acid solution by adding dilute hydrochloric acid in neutral area prevents chlorine gas generation, which is generated under pH 7 or less (see FIG. 1).

Example 1

(Hypochlorous Acid Aqueous Solution and Preparation Example Thereof)

Sodium hypochlorite is weighed so as to be the range from 0.026 w/v %, and mixed with purified water to prepare sodium hypochlorite solution by dilution. The sodium hypochlorite solution prepared by the dilution is justified so as to have pH 6.0 to 6.5 by using dilute hydrochloric acid (about 9.5 to 10.5 w/v %). Thus prepared solution contains 220 ppm of effective chlorine concentration.

(Component Analysis of the Hypochlorous Acid Aqueous Solution)

Herein below, the table for the component analysis of the hypochlorous acid aqueous solution is shown.

TABLE 1

Figure 1:
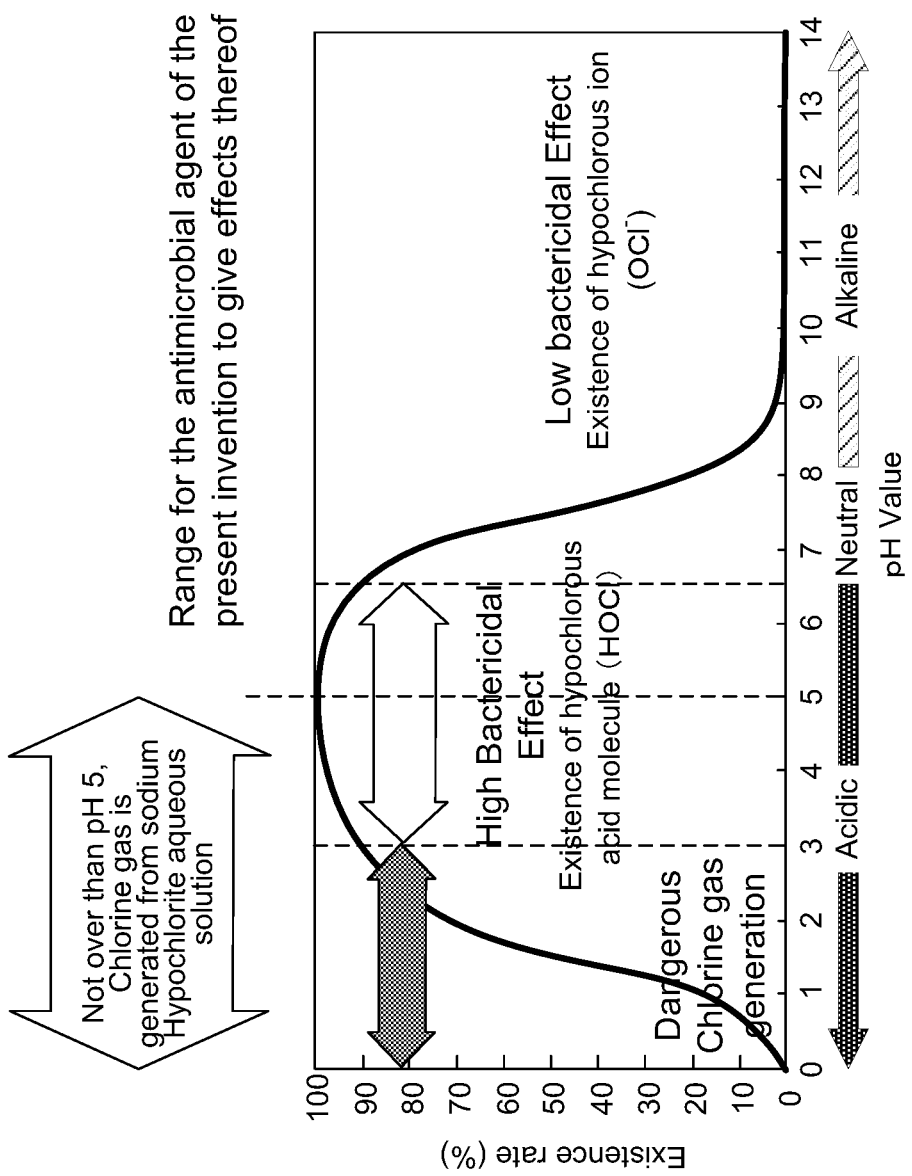
FIG. 1 is a graph showing summarized difference of chlorine gas generation at each pH area between aqueous sodium hypochlorite solution and the aqueous hypochlorous acid solution pf the present invention.
Figure 4:
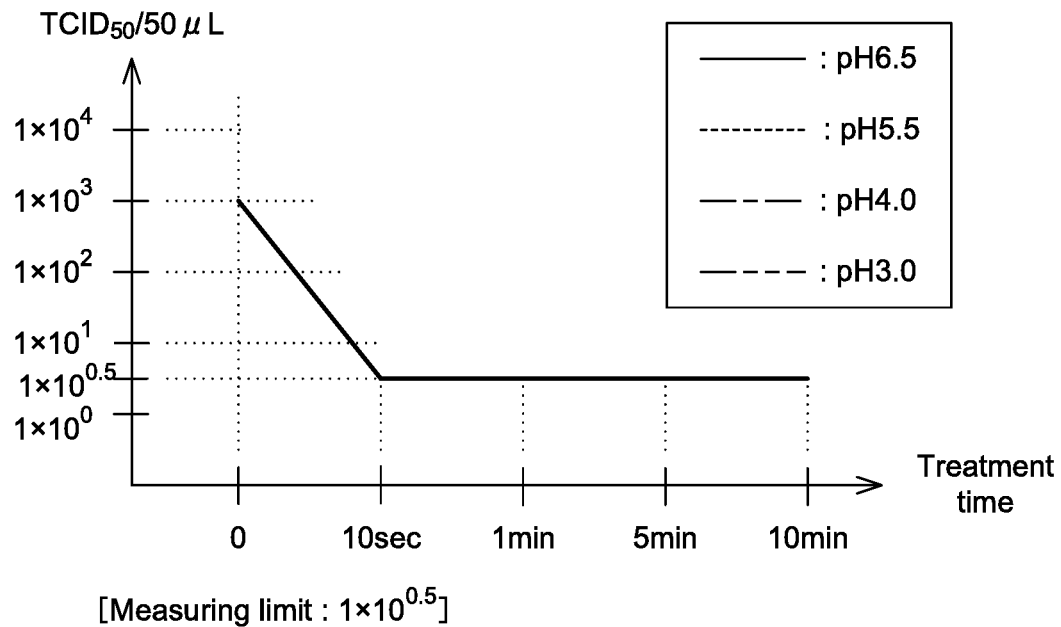
FIG. 4 is a graph showing antiviral effect for Feline panleukemia virus (Feline panleukemia virus) ATCC VR-648.
Figure 5:
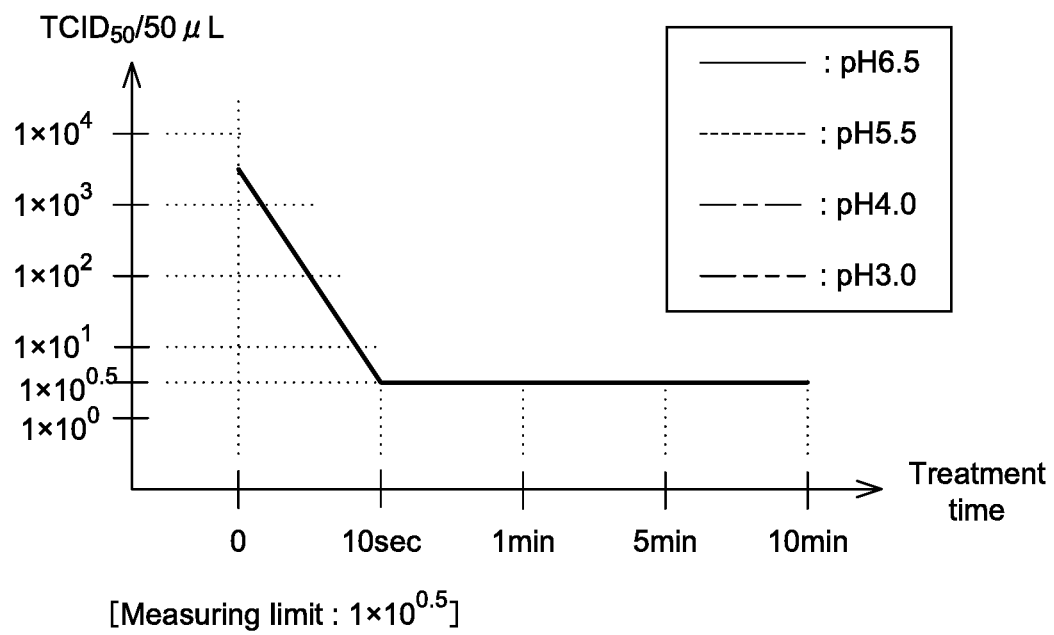
Figure 8:
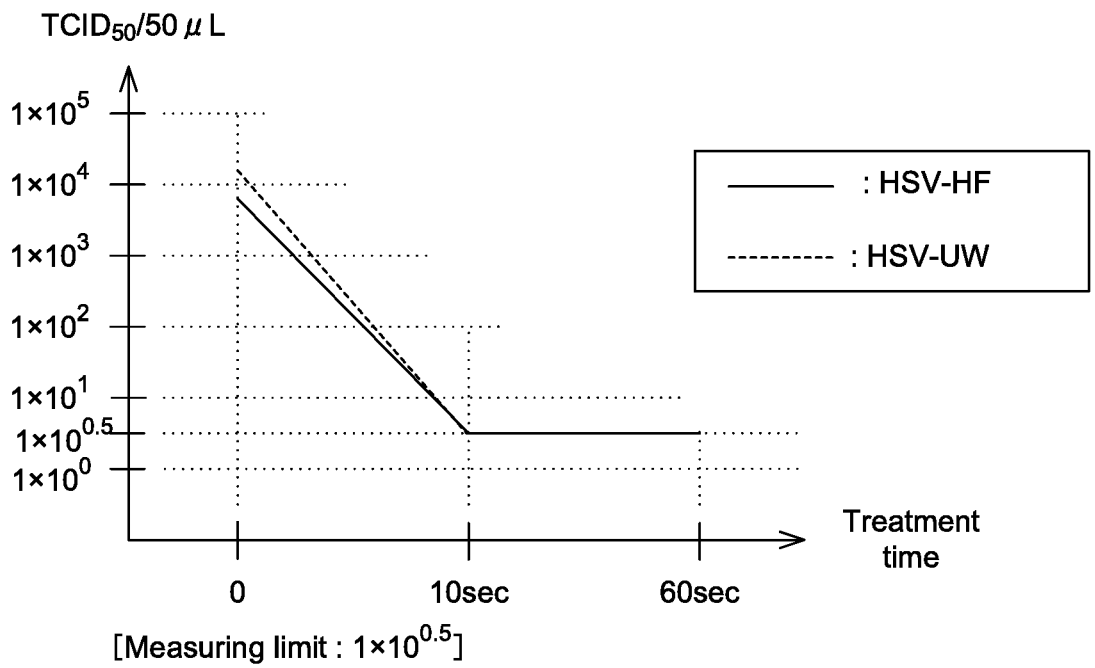
Figure 9:
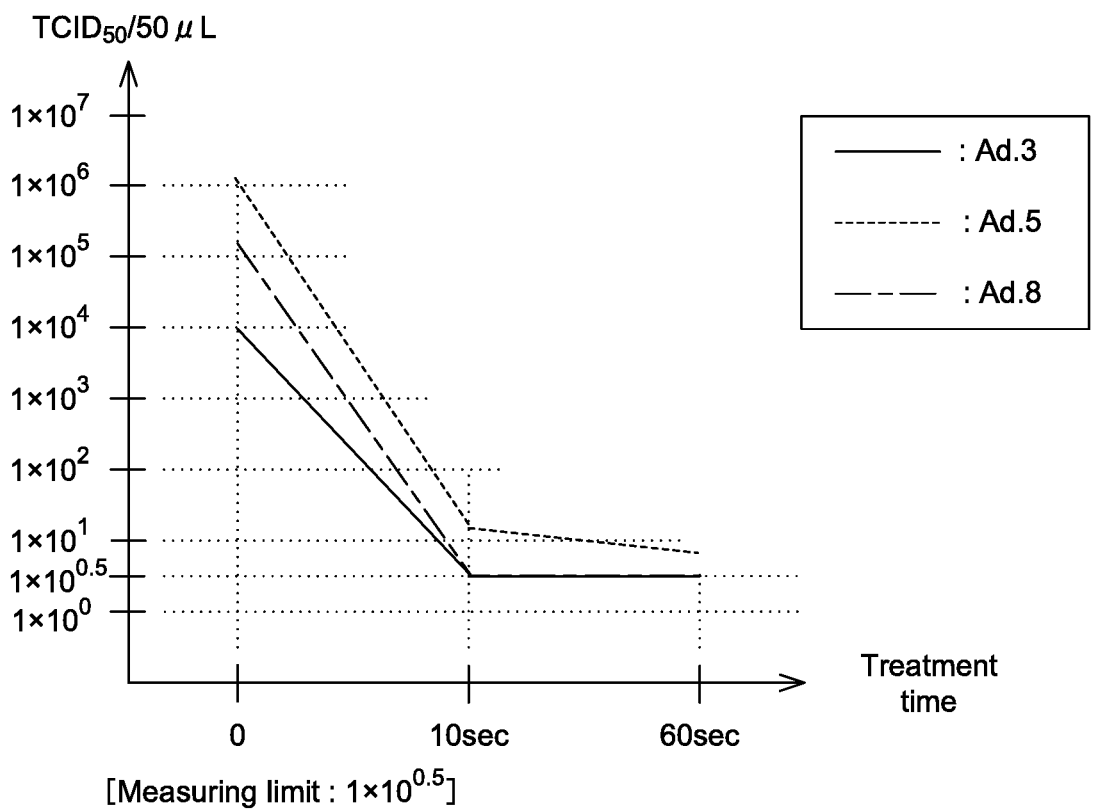

|  |  |  | Lot Nos. | |
|---|---|---|---|---|---|
| Items to be checked | Specifications |  | 001 | 002 | 003 |
| Properties | The product is yellow colored liquid without odor, or with faint chlorine odor. |  | OK | OK | OK |
| Validation Test | (1) When 1 mL of sodium hydroxide (2,500 times diluted), and 0.2 mL of potassium iodide test solution are added to 5 mL of the product, the solution turns yellow. When 0.5 mL of starch test solution is further added to the solution, the solution turns deep blue. |  | OK | OK | OK |
|  | (2) When the 0.1 mL of the permanganate solution (300 times diluted) is added into 5 mL of the product and 1 mL of diluted sulfuric acid (20 times diluted) is added. After that, when 1 mL of the diluted sulfuric acid is further added thereto, red-purple color of the solution is unfaded. |  | OK | OK | OK |
|  | (3) The solution prepared by adding 90 mL of the product and 10 mL of sodium hydroxide solution (5 times diluted) has absorption maximum from the wavelength between 290 to 294 nm. |  | OK | OK | OK |
| Purity Test pH | from 4.5 to 6.5 | No. 1 | 6.4 | 6.4 | 6.4 |
|  |  | 2 | 6.4 | 6.4 | 6.4 |
|  |  | 3 | 6.4 | 6.4 | 6.4 |
| Total Residue | not more than 0.25% | No. 1 | 0.03 | 0.03 | 0.03 |
| Quantitative Value | 220 ± 40 ppm | No. 1 | 256.0 | 259.2 | 251.1 |
|  |  | 2 | 255.5 | 259.5 | 251.4 |
|  |  | 3 | 255.6 | 259.2 | 250.9 |

Also, the purified water used in the present invention has following characteristics:

TABLE 2

| Item | Characteristics & properties |
|---|---|
| Properties | Colorless and odorless liquid |
| Purity | Not over than 0.50 mg/L under test for total organic carbon content ≤0.50 mg/L |
| Conductivity | Conductivity at 25° C. is not over than 2.1 µS/cm |

* Conductivity test: adequate amount of the purified water is poured into a beaker and then stirred. Temperature of the purified water is adjusted at 25 ± 1° C., and the conductivity pf the water is measured at regular intervals, vigorously stirring the water. The conductivity of the purified water (25° C.) is set the value when change in conductivity/5 minutes becomes not over than 0.1 µS/cm.

Example 2

(Determination of Antiviral Effect Against Norovirus)
(1) Test Strain
Norovirus, which is belonging to NV gene group 2, derived from feces was used. The virus was qualitatively confirmed according to a detection method for Norovirus, PCR method, recommended by ministry of health, labor and welfare.
(2) Preparation of Test Samples
In order to prepare the test samples, the aqueous hypochlorite acid solution is diluted so as to be the effective chlorine concentration at 200 ppm. The following samples are prepared by using the above-mentioned test samples to be used for measurement of the antiviral effects.
  (a) Negative control (500 µL of Norovirus suspension)
  (b) Positive control (5× dilution: 100 µL of Norovirus suspension+400 µL of purified water)
  (c) Test samples (100 µL of Norovirus suspension+400 µL of the test sample)
(3) Determination Method
Growth of norovirus was confirmed by using PCR. Firstly, three test samples as escribed above were mixed by using vortex mixer. Then, the samples were stood for 15 minutes at room temperature, and extracted nucleic acid (RNA) according to RT-PCR. After that, RNA was obtained with DNase to delete contaminants. The obtained RNA was amplified by using PCR kit (ReverTra-Plus, Toyobo) at room temperature to obtain final products.

20 µg of the obtained final products was subjected to 2.5% agarose gel electrophoresis (100 V, 50 minutes) to confirm the amplification of norovirus DNA. Results were shown in the following Table 3.

TABLE 3

| Sample from | Sample | Results |
|---|---|---|
| Reference 1 | (a) | Positive (+) |
| Reference 2 | (b) | Positive (+) |
| Test 1 | (c)1 | Negative (−) |
| Test 2 | (c)2 | Negative (−) |

As shown in Table 3, growth of norovirus was observed in control section. However, it was not observed in test sections. Accordingly, the aqueous hypochlorous acid solution of the present invention has virucidal activity against norovirus.

Example 3

(Determination of Bactericidal Effect Against Bacteria)
(1) Test Samples
In order to prepare the test samples, the aqueous hypochlorous acid solution prepared in Example 1 was utilized as the undiluted solution. The effective chlorine concentration of undiluted solution was 200 ppm. By performing serial doubling dilution, the test samples were prepared and utilized the determination; the effective chlorine concentrations of the test samples were 100 ppm, 50 ppm, 25 ppm, 12.5 ppm and 6.3 ppm.

(2) Test Method
1) Test Bacteria

Seven kinds of bacteria shown at the table 4 were used as the test bacteria. Undiluted solution having 200 ppm of the effective chlorine concentration is diluted to prepare 2-fold serial dilution to obtain the diluted ablutions having 100 ppm, 50 ppm, 25 ppm, 12.5 ppm, or 6.3 ppm. They are dispensed 5 mL each into 20 mL volume of test tubes. The effective chlorine concentrations in the samples were measured by using Handy Water Meter, Model AQ-101 (Shibata Scientific Technology Ltd.).

TABLE 4

Minimal bactericidal conc. At each timepoint (ppm)

| Bacteria to be tested | Treatment time (min.) | | | | |
|---|---|---|---|---|---|
| | 0.5 | 1 | 2 | 5 | 10 |
| | Minimal bactericidal conc. at each time point (ppm) | | | | |
| Escherichia coli (E. coli) | 25 | 25 | 12.5 | 12.5 | 12.5 |
| Staphylococcus aureus (S. aureus) | 25 | 25 | 12.5 | <6.3 | <6.3 |
| Bacillus subtilis (N. subtills) | 100 | 100 | 100 | 100 | 100 |
| Serratia liquefaciencei (S. liquefaciencei) | 25 | 25 | 12.5 | <6.3 | <6.3 |
| Salmonella Enteritidis (S. Enteritidis) | 25 | 12.5 | 12.5 | 12.5 | 12.5 |
| Listeria monocytogenes (L. monocytogenes) | 12.5 | 12.5 | 12.5 | 12.5 | 12.5 |
| Pseudomonas aeruginosa (P. aeruginosa) | 12.5 | 12.5 | 12.5 | 12.5 | <6.3 |

2) Pre-Culture Before Test

Tryptic Soy Broth (Tryptic Soy Broth, it is sometimes referred to as "TSB" herein below.) is used as the medium, the test bacteria are subjected to standing culture (pre-culture) at 35° C. for 20 to 24 hours, and then is subjected to the teat. Numbers of the cultured bacteria were in the range between $1 \times 10^7$ to $1 \times 10^8$.

3) Test Method 0.1 mL of the solutions containing the bacteria, which is referred to as "microbe fluid", shown in Table 4 are respectively inoculated into the samples and then mixed to prepare test samples. After inoculation, 0.1 mL portion of each sample are taken out at each time point (0.5 minutes, 1 minute, 2 minutes, 5 minutes, and 10 minutes), and then the portion is respectively inoculated in 2 mL TSB for diluted solution to prepare a diluted solution to prepare the diluted solution, respectively. Furthermore, another 0.1 mL portion is taken from TSB to which the microbe is inoculated, and it is streaked on the agar plate containing SA medium. The streaked agar plates are incubated at 35° C. for 24 hours, and then appeared colonies are counted.

4) Determination

The appeared colony numbers are counted by concentrations of the samples to obtain viable microbe numbers at each time point for determining microbicidal effects.

(3) Test Results

The bacterial numbers at minimum bactericidal concentration are shown in Table 4.

The following Tables 5 and 6 show these in effective chlorine concentration. In these Tables, + represents growth (colony formation found), − represents no-growth (no colony formation not found).

TABLE 5

Disinfection time (minutes)

| | Effective chlorine concentration (ppm) | Treatment time (min.) | | | | |
|---|---|---|---|---|---|---|
| | | 0-0.1 | 0.5 | 1 | 2 | 5 | 10 |
| E. coli | 50 | − | − | − | − | − | − |
| | 25 | − | − | − | − | − | − |
| | 12.5 | + | + | + | − | − | − |
| | 6.3 | + | + | + | + | + | + |
| S. aureus | 50 | − | − | − | − | − | − |
| | 25 | + | − | − | − | − | − |
| | 12.5 | + | + | + | − | − | − |
| | 6.3 | + | + | + | + | − | − |
| N. subtills | 200 | − | − | − | − | − | − |
| | 100 | − | − | − | − | − | − |
| | 50 | + | + | + | + | + | + |
| | 25 | + | + | + | + | + | + |
| | 12.5 | + | + | + | + | + | + |
| | 6.3 | + | + | + | + | + | + |

TABLE 6

Disinfection time of bacteria

| | Effective chlorine concentration (ppm) | Treatment time (min.) | | | | |
|---|---|---|---|---|---|---|
| | | 0-0.1 | 0.5 | 1 | 2 | 5 | 10 |
| S. liquefaciencei | 50 | − | − | − | − | − | − |
| | 25 | − | − | − | − | − | − |
| | 12.5 | + | + | + | − | − | − |
| | 6.3 | + | + | + | + | − | − |
| S. Enteritidis | 50 | − | − | − | − | − | − |
| | 25 | − | − | − | − | − | − |
| | 12.5 | + | + | − | − | − | − |
| | 6.3 | + | + | + | + | + | + |
| L. monocytogenes | 50 | − | − | − | − | − | − |
| | 25 | − | − | − | − | − | − |
| | 12.5 | − | − | − | − | − | − |
| | 6.3 | + | + | + | + | + | + |
| P. aeruginosa | 50 | − | − | − | − | − | − |
| | 25 | − | − | − | − | − | − |
| | 12.5 | − | − | − | − | − | − |
| | 6.3 | + | + | + | + | + | − |

As a result of the minimum bactericidal test using 7 bacteria shown in Table 4, the colony formation of 6 bacteria other than Bacillus subtilis (Bacillus subtilis) is not observed after 2 minutes treatment by using the solution containing the effective chlorine concentration not less than 12.5 ppm. Therefore, it was determined that they were disinfected.

Particularly, the aqueous hypochlorous acid solution has strong effect against Pseudomonas aeruginosa, of which colony formation is not observed by the treatment of the solution containing not less than 12.5 ppm of the effective chlorine concentration not less than 0.1 minutes. This was determined that the bacteria were disinfected.

Bacillus subtilis (Bacillus subtilis) is solely form spores among 7 bacteria tested. The reason why Bacillus subtilis is not disinfected by using the solution containing high effective chlorine concentration, 100 ppm was thought that they formed the spores. In general, it is said that the spore is resistant to heat, the disinfection against, ultraviolet ray or dryness, however, it is also resistant against the aqueous hypochlorous acid solution.

Example 4

(Determination of Effects Against Bacteria, Yeast and Fungi)
(1) Sample to be Tested Original solution having 200 to 210 ppm as effective chlorine concentration is diluted 2-fold or 4-fold dilution by using sterilized distilled water to prepare the diluent having 100 to 103 ppm as the effective chlorine concentration (hereinbelow, it is referred to as "×2 diluent".) and that having 50 to 52 ppm as the effective chlorine concentration (hereinbelow, it is referred to as "×4 diluent".). Then, 10 mL of each diluents are dispensed into 15 mL volume test tube to be tested. The effective chlorine concentration is determined by using Handy water analyzer AQ-101 (Shibata Scientific Technology Ltd.). Also, measurement time is set at 30 second, 60 second, 5 minutes, and 10 minutes, and the measurement time of ×4 diluent is solely extended to 30 minutes.

(2) Test Methods
(2-1) Bacteria to be Tested

Four bacteria strains, 2 yeast strain, and 8 fungi strains shown in the following table 7 are employed for conducting tests by using agar plate or liquid medium. Here in below, the bacteria, yeast, or fungi (filamentous fungi) are sometimes collectively referred to as "test microbes".

(2-2) Pre-Culture

The test microbes shown in Table 7 are pre-cultured under the following conditions, and then subjected to tests. The pre-culture of the bacteria is conducted at 37° C. for 24 hours by using SA medium. The pre-culture of the yeast is conducted at 25° C. for 48 hours by using potato dextrose (PDA) medium. The pre-culture of the fungi (the filamentous fungi) is conducted at 25° C. for 7 to 10 days by using PDA medium.

(2-3) Preparation of a Suspension Contains the Microbes

Among the test microbes pre-cultured as described above, the suspension containing the bacteria or the yeast is prepared to become the concentration from $1 \times 10^5$ to $1 \times 10^6$ CFU/mL by using sterilized saline. Also, the fungi (the filamentous fungi) is prepared at the concentration from $1 \times 10^5$ to $1 \times 10^6$ CFU/mL by using saline including 0.05% Tween 80.

(2-4) Test Methods

Effects of the hypochlorous acid aqueous solution against the test microbe listed on the following Table 7 is studied by using the agar plate or liquid medium. 0.1 mL of the suspension containing the microbe is inoculated into 10 mL of samples dispensed into 15 mL size of test tubes, and the tubes are stood at room temperature for contacting with the samples. At the predetermined time points (30 seconds, 60 seconds, 5 minutes, 10 minutes, and 30 minutes only for ×4 diluted sample), antiseptic sampling of 0.1 mL from each sample is conducted to prepare serial dilutions by using sterilized saline to prepare the growth test sample. When the test sample containing bacteria is streaked on SA medium, and both of those containing the yeast or the fungi are streaked on PDA medium. The agar plates on which each sample is streaked are incubated: at 35° C. for 2 days for the bacteria: at 25° C. for 2 days for the yeast; and 25° C. for 7 days for the fungi.

(2-4-2) the Test Using Liquid Medium 0.1 mL of the test microbe suspension, which is prepared as the same as those used for the agar plates, is inoculated into 10 mL of the test sample, and stood at room temperature. Then, o.1 mL of sampling is conducted from each sample at the predetermined time points (30 seconds, or 60 seconds from the start. The test bacteria are inoculated into 10 mL of the liquid medium (soybean-casein digest medium, herein below, it is referred to as "SCD medium".) to prepare the test sample. The test yeast or the test fungi is inoculated is also inoculated in glucose-peptone medium (hereinbelow, it is referred to as "GP medium") at the starting cell numbers shown in the following Tables 7 to 12 to prepare teach test sample.

From each test sample, 1 mL portion is taken for further dilution, and then they are inoculated in each of the medium as described above. ACD medium to which the bacteria are inoculated are incubated at 35° C. for 2 days. GP medium to which the yeast is inoculated at 25° C. for 2 hours; and GP medium to which the fungi are inoculated is incubated at 25° C. for 7 days.

(2-5) Determination

In the test using agar plates, appeared colony numbers are counted by concentrations of the samples to obtain viable microbe numbers at each time point for determining microbicidal effects. In the test using the liquid medium, growth of the microbe is observed and determined by using both of colony formation and visual observation.

(3) Test Results

The bacterial numbers at each time point in the test using the agar plate are shown in Tables 7 to 9. Also, these in the test using the liquid medium are shown in Tables 10 to 12. In these Tables, + represents growth (colony formation found), − represents no-growth (no colony formation not found).

Also, in Tables 7 to 12, the description of *Escherichia coli* or *E. coli* represents a strain, *Escherichia coli* KEC-B-001: that of *Staphylococcus aureus* or *S. aureus* represents the strain, *Staphylococcus aureus* KEC-B-002; that of *Serratia* sp. represents the strain, *Serratia* sp. THMC 56; that of *Bacillus subtills* or *B. subtills* represents the strain, *Bacillus subtills* KEC-B-007, respectively.

The description of *Candida albicans* or *C. albicans* represents the strain, *Candida albicans* HRC 032; that of *Rhodotorula* sp. represents the strain, *Rhodotorula* sp. HRC 042, respectively.

The description of *Cladosporium cladosporioides* or *C. cladosporioides* represents *Cladosporium cladosporioides* HRC 219; that of *Altrnaria alternate* or *A. alternate* represents the strain, *Altrnaria alternate* HRC 237; that of *Penicillium glabrum* or *P. glabrum* represents the strain, *Penicillium glabrum* HRC 659; that of *Aspergillus niger* or *A. niger* represents the strain, *Aspergillus niger* HRC 258; that of *Chaetomium* sp. represents the strain, *Chaetomium* sp. HRC 280; that of *Fusarium* sp. represents the strain, *Fusarium* sp. HRC 289; that of *Emericella nidulans* or E. *nidulans* represents the strain *Emericella nidulans* HRC 210; that of *Neosartorya* sp. represents the strain, *Neosartorya* sp. HRC 259, respectively.

TABLE 7

Agar plate: Viable microbe numbers at each time point (dilution rate = 1, effective chlorine concentration = 200 to 210 ppm)

| | | \multicolumn{6}{c}{Treatment time (min.)} | |
|---|---|---|---|---|---|---|---|---|
| | Microbes used | 0 Starting No. | 0.5 | 1 | 5 | 10 | 30 | Decision (min.)* |
| | | | \multicolumn{5}{c}{Viable microbe numbers} | | |
| Bacteria | E. coli | $7.8 \times 10^5$ | $<\times 10^1$ | $<\times 10^1$ | $<\times 10^1$ | – | – | <0.5 |
| | S. aureus | $2.1 \times 10^5$ | $<\times 10^1$ | $<\times 10^1$ | $<\times 10^1$ | – | – | <0.5 |
| | Serratia sp. | $5.2 \times 10^5$ | $<\times 10^1$ | $<\times 10^1$ | $<\times 10^1$ | – | – | <0.5 |
| | B. subtills | $5.6 \times 10^5$ | $<\times 10^1$ | $<\times 10^1$ | $<\times 10^1$ | – | – | <0.5 |
| Yeast | C. albicans | $2.4 \times 10^6$ | $<\times 10^1$ | $<\times 10^1$ | $<\times 10^1$ | $<\times 10^1$ | – | <0.5 |
| | Rhodotorula sp. | $6.4 \times 10^5$ | $<\times 10^1$ | $<\times 10^1$ | $<\times 10^1$ | $<\times 10^1$ | – | <0.5 |
| Fungi | C. cladosporioides | $1.1 \times 10^5$ | $<\times 10^1$ | $<\times 10^1$ | $<\times 10^1$ | $<\times 10^1$ | – | <0.5 |
| | A. alternate | $7.3 \times 10^4$ | $<\times 10^1$ | $<\times 10^1$ | $<\times 10^1$ | $<\times 10^1$ | – | <0.5 |
| | P. glabrum | $5.3 \times 10^4$ | $<\times 10^1$ | $<\times 10^1$ | $<\times 10^1$ | $<\times 10^1$ | – | <0.5 |
| | A. niger | $2.0 \times 10^4$ | $<\times 10^1$ | $<\times 10^1$ | $<\times 10^1$ | $<\times 10^1$ | – | <0.5 |
| | Chaetomium sp. | $1.2 \times 10^4$ | $1.5 \times 10^4$ | $1.5 \times 10^4$ | $1.2 \times 10^4$ | $1.2 \times 10^4$ | – | >10 |
| | Fusarium sp. | $2.2 \times 10^4$ | $<\times 10^1$ | $<\times 10^1$ | $<\times 10^1$ | $<\times 10^1$ | – | <0.5 |
| | Emericella nidulans | $1.6 \times 10^4$ | $<\times 10^1$ | $<\times 10^1$ | $<\times 10^1$ | $<\times 10^1$ | – | <0.5 |
| | Neosartorya sp. | $1.6 \times 10^4$ | $<\times 10^1$ | $<\times 10^1$ | $<\times 10^1$ | $<\times 10^1$ | – | <0.5 |

*Disinfection time
Unit: CFU/mL

TABLE 8

Agar plate: Viable microbe numbers at each time point (dilution rate = 2, effective chlorine concentration = 100 to 103 ppm)

| | | \multicolumn{6}{c}{Treatment time (min.)} | |
|---|---|---|---|---|---|---|---|---|
| | Microbes used | 0 Starting No. | 0.5 | 1 | 5 | 10 | 30 | Decision (min.)* |
| | | | \multicolumn{5}{c}{Viable microbe numbers} | | |
| Bacteria | E. coli | $7.8 \times 10^5$ | $<\times 10^1$ | $<\times 10^1$ | $<\times 10^1$ | – | – | <0.5 |
| | S. aureus | $2.1 \times 10^5$ | $<\times 10^1$ | $<\times 10^1$ | $<\times 10^1$ | – | – | <0.5 |
| | Serratia sp. | $5.2 \times 10^5$ | $<\times 10^1$ | $<\times 10^1$ | $<\times 10^1$ | – | – | <0.5 |
| | B. subtills | $5.6 \times 10^5$ | $<\times 10^1$ | $<\times 10^1$ | $<\times 10^1$ | – | – | <0.5 |
| Yeast | C. albicans | $2.4 \times 10^6$ | $<\times 10^1$ | $<\times 10^1$ | $<\times 10^1$ | $<\times 10^1$ | – | <0.5 |
| | Rhodotorula sp. | $6.4 \times 10^5$ | $<\times 10^1$ | $<\times 10^1$ | $<\times 10^1$ | $<\times 10^1$ | – | <0.5 |
| Fungi | C. cladosporioides | $1.1 \times 10^5$ | $<\times 10^1$ | $<\times 10^1$ | $<\times 10^1$ | $<\times 10^1$ | – | <0.5 |
| | A. alternate | $7.3 \times 10^4$ | $<\times 10^1$ | $<\times 10^1$ | $<\times 10^1$ | $<\times 10^1$ | – | <0.5 |
| | P. glabrum | $5.3 \times 10^4$ | $<\times 10^1$ | $<\times 10^1$ | $<\times 10^1$ | $<\times 10^1$ | – | <0.5 |
| | A. niger | $2.0 \times 10^4$ | $1.3 \times 10^3$ | $5.6 \times 10^2$ | $<\times 10^1$ | $<\times 10^1$ | – | <0.5 |
| | Chaetomium sp. | $1.2 \times 10^4$ | $2.1 \times 10^4$ | $1.6 \times 10^4$ | $1.0 \times 10^4$ | $5.2 \times 10^3$ | – | >10 |
| | Fusarium sp. | $2.2 \times 10^4$ | $<\times 10^1$ | $<\times 10^1$ | $<\times 10^1$ | $<\times 10^1$ | – | <0.5 |
| | Emericella nidulans | $1.6 \times 10^4$ | $<\times 10^1$ | $<\times 10^1$ | $<\times 10^1$ | $<\times 10^1$ | – | <0.5 |
| | Neosartorya sp. | $1.6 \times 10^4$ | $<\times 10^1$ | $<\times 10^1$ | $<\times 10^1$ | $<\times 10^1$ | – | <0.5 |

*Disinfection time
Unit: CFU/mL

TABLE 9

Agar plate: Viable microbe numbers at each time point (dilution rate = 4, effective chlorine concentration = 50 to 52 ppm)

| | | \multicolumn{6}{c}{Treatment time (min.)} | |
|---|---|---|---|---|---|---|---|---|
| | Microbes used | 0 Starting microbe No. | 0.5 | 1 | 5 | 10 | 30 | Decision (min.)* |
| | | | \multicolumn{5}{c}{Viable microbe numbers} | | |
| Bacteria | E. coli | $7.8 \times 10^5$ | $<\times 10^1$ | $<\times 10^1$ | $<\times 10^1$ | – | – | <0.5 |
| | S. aureus | $2.1 \times 10^5$ | $<\times 10^1$ | $<\times 10^1$ | $<\times 10^1$ | – | – | <0.5 |
| | Serratia sp. | $5.2 \times 10^5$ | $<\times 10^1$ | $<\times 10^1$ | $<\times 10^1$ | – | – | <0.5 |
| | B. subtills | $5.6 \times 10^5$ | $<\times 10^1$ | $<\times 10^1$ | $<\times 10^1$ | – | – | <0.5 |
| Yeast | C. albicans | $2.4 \times 10^6$ | $<\times 10^1$ | $<\times 10^1$ | $<\times 10^1$ | $<\times 10^1$ | $<\times 10^1$ | <0.5 |
| | Rhodotorula sp. | $6.4 \times 10^5$ | $<\times 10^1$ | $<\times 10^1$ | $<\times 10^1$ | $<\times 10^1$ | $<\times 10^1$ | <0.5 |
| Fungi | C. cladosporioides | $1.1 \times 10^5$ | $<\times 10^1$ | $<\times 10^1$ | $<\times 10^1$ | $<\times 10^1$ | $<\times 10^1$ | <0.5 |
| | A. alternate | $7.3 \times 10^4$ | $<\times 10^1$ | $<\times 10^1$ | $<\times 10^1$ | $<\times 10^1$ | $<\times 10^1$ | <0.5 |
| | P. glabrum | $5.3 \times 10^4$ | $<\times 10^1$ | $<\times 10^1$ | $<\times 10^1$ | $<\times 10^1$ | $<\times 10^1$ | <0.5 |

TABLE 9-continued

Agar plate: Viable microbe numbers at each time point (dilution rate = 4, effective chlorine concentration = 50 to 52 ppm)

| | | Treatment time (min.) | | | | | |
|---|---|---|---|---|---|---|---|
| Microbes used | Starting microbe No. | 0.5 | 1 | 5 | 10 | 30 | Decision (min.)* |
| | | Viable microbe numbers | | | | | |
| A. niger | $2.0 \times 10^4$ | $7.2 \times 10^2$ | $1.4 \times 10^2$ | $<\times 10^1$ | $<\times 10^1$ | $<\times 10^1$ | <0.5 |
| Chaetomium sp. | $1.2 \times 10^4$ | $1.9 \times 10^4$ | $1.7 \times 10^4$ | $2.0 \times 10^4$ | $9.2 \times 10^3$ | $7.7 \times 10^3$ | >30 |
| Fusarium sp. | $2.2 \times 10^4$ | $<\times 10^1$ | $<\times 10^1$ | $<\times 10^1$ | $<\times 10^1$ | $<\times 10^1$ | <0.5 |
| Emericella nidulans | $1.6 \times 10^4$ | $<\times 10^1$ | $<\times 10^1$ | $<\times 10^1$ | $<\times 10^1$ | $<\times 10^1$ | <0.5 |
| Neosartorya sp. | $1.6 \times 10^4$ | $<\times 10^1$ | $<\times 10^1$ | $<\times 10^1$ | $<\times 10^1$ | $<\times 10^1$ | <0.5 |

*Disinfection time
Unit: CFU/mL

In any concentrations, both of the disinfection time of 4 bacteria and 2 yeasts described above are not over than 0.5 minutes. Also, that of the fungi is not over than 0.5 minutes except Chaetomium.

Followings show effects against respective microbes using the liquid medium. Even if the liquid medium is used, 0.1 mL portion of the medium is taken out from the sample at each treatment time, and then streaked on the same agar plate to obtain viable bacteria numbers from formed colony numbers.

TABLE 10

Liquid medium: effective chlorine concentration 200-210 ppm

| | | Dilution rate | | | | | |
|---|---|---|---|---|---|---|---|
| | | ×10 | ×100 | ×10 | ×100 | ×10 | ×100 |
| | | Treatment time (min.) | | | | Decision Disinfection | |
| Microbes used | Starting Microbe No. | 0.5 | | 1 | | time (min.) | |
| Bacteria E. coli | $7.8 \times 10^5$ | − | − | − | − | <0.5 | <0.5 |
| S. aureus | $2.1 \times 10^5$ | − | − | − | − | <0.5 | <0.5 |
| Serratia sp. | $5.2 \times 10^5$ | − | − | − | − | <0.5 | <0.5 |
| B. subtills | $5.6 \times 10^5$ | − | − | − | − | <0.5 | <0.5 |
| Yeast C. albicans | $7.6 \times 10^5$ | − | − | − | − | <0.5 | <0.5 |
| Rhodotorula sp. | $4.1 \times 10^5$ | − | − | − | − | <0.5 | <0.5 |
| Fungi C. cladosporioides | $1.1 \times 10^5$ | − | − | − | − | <0.5 | <0.5 |
| A. alternate | $7.3 \times 10^4$ | − | − | − | − | <0.5 | <0.5 |
| P. glabrum | $5.3 \times 10^4$ | − | − | − | − | <0.5 | <0.5 |
| A. niger | $2.0 \times 10^4$ | + | + | + | − | 1 | 0.5 |
| Chaetomium sp. | $1.2 \times 10^4$ | + | + | + | + | >1 | >1 |
| Fusarium sp. | $2.2 \times 10^4$ | − | − | − | − | <0.5 | <0.5 |
| Emericella nidulans | $1.6 \times 10^4$ | − | − | − | − | <0.5 | <0.5 |
| Neosartorya sp. | $1.6 \times 10^4$ | − | − | − | − | <0.5 | <0.5 |

Unit: CFU/mL

TABLE 11

Liquid medium: effective chlorine concentration 100-103 ppm

| | | Dilution rate | | | | | |
|---|---|---|---|---|---|---|---|
| | | ×10 | ×100 | ×10 | ×100 | ×10 | ×100 |
| | | Treatment time (min.) | | | | Decision Disinfection | |
| Microbes used | Starting Microbe No. | 0.5 | | 1 | | time (min.) | |
| Bacteria E. coli | $7.8 \times 10^5$ | − | − | − | − | <0.5 | <0.5 |
| S. aureus | $2.1 \times 10^5$ | − | − | − | − | <0.5 | <0.5 |
| Serratia sp. | $5.2 \times 10^5$ | − | − | − | − | <0.5 | <0.5 |
| B. subtills | $5.6 \times 10^5$ | − | − | − | − | <0.5 | <0.5 |
| Yeast C. albicans | $7.6 \times 10^5$ | − | − | − | − | <0.5 | <0.5 |
| Rhodotorula sp. | $4.1 \times 10^5$ | − | − | − | − | <0.5 | <0.5 |

TABLE 11-continued

Liquid medium: effective chlorine concentration 100-103 ppm

| | | | Dilution rate | | | | | |
|---|---|---|---|---|---|---|---|---|
| | | | ×10 | ×100 | ×10 | ×100 | ×10 | ×100 |
| | | | Treatment time (min.) | | | | Decision Disinfection |  |
| | Microbes used | Starting Microbe No. | 0.5 | | 1 | | time (min.) | |
| Fungi | C. cladosporioides | $1.1 \times 10^5$ | − | − | − | − | <0.5 | <0.5 |
| | A. alternate | $7.3 \times 10^4$ | − | − | − | − | <0.5 | <0.5 |
| | P. glabrum | $5.3 \times 10^4$ | − | − | − | − | <0.5 | <0.5 |
| | A. niger | $2.0 \times 10^4$ | + | + | + | + | >1 | >1 |
| | Chaetomium sp. | $1.2 \times 10^4$ | + | + | + | + | >1 | >1 |
| | Fusarium sp. | $2.2 \times 10^4$ | − | − | − | − | <0.5 | <0.5 |
| | Emericella nidulans | $1.6 \times 10^4$ | − | − | − | − | <0.5 | <0.5 |
| | Neosartorya sp. | $1.6 \times 10^4$ | − | − | − | − | <0.5 | <0.5 |

Unit: CFU/mL

TABLE 12

Liquid medium: effective chlorine concentration 50-52 ppm

| | | | Dilution rate | | | | | |
|---|---|---|---|---|---|---|---|---|
| | | | ×10 | ×100 | ×10 | ×100 | ×10 | ×100 |
| | | | Treatment time (min.) | | | | Decision Disinfection | |
| | Microbes used | Starting Microbe No. | 0.5 | | 1 | | time (min.) | |
| Bacteria | E. coli | $7.8 \times 10^5$ | − | − | − | − | <0.5 | <0.5 |
| | Staphyl. aureus | $2.1 \times 10^5$ | − | − | − | − | <0.5 | <0.5 |
| | Serratia | $5.2 \times 10^5$ | − | − | − | − | <0.5 | <0.5 |
| | Bacillus subtills | $5.6 \times 10^5$ | − | − | − | − | <0.5 | <0.5 |
| Yeast | Candida albicans | $7.6 \times 10^5$ | − | − | − | − | <0.5 | <0.5 |
| | Rhodotorula | $4.1 \times 10^5$ | − | − | − | − | <0.5 | <0.5 |
| Fungi | C. cladosporioides | $1.1 \times 10^5$ | + | − | − | − | 0.5 | 0.5 |
| | Altrnaria | $7.3 \times 10^4$ | + | − | − | − | 0.5 | 0.5 |
| | Penicillium | $5.3 \times 10^4$ | − | − | − | − | <0.5 | <0.5 |
| | A. niger | $2.0 \times 10^4$ | + | + | + | + | >1 | >1 |
| | Chaetomium | $1.2 \times 10^4$ | + | + | + | + | >1 | >1 |
| | Fusarium | $2.2 \times 10^4$ | − | − | − | − | <0.5 | <0.5 |
| | Emericella nidulans | $1.6 \times 10^4$ | − | − | − | − | <0.5 | <0.5 |
| | Neosartorya fischeri | $1.6 \times 10^4$ | − | − | − | − | <0.5 | <0.5 |

Unit: CFU/mL

In the test by using the liquid medium, there were some differences in the disinfection time of Fungi depending on the effective chlorine concentrations. Other than that, the microbes were quickly died by using any hypochlorous aqueous solution with any dilution rates, and this showed that the hypochlorous aqueous solution has the sterilization effects against the microbes.

The hypochlorous aqueous solution of the present invention is prepared by solely adding the purified water into the weak acidic hypochlorous aqueous solution. Also, it has an approval of the regulatory authorities as a medicine so that it is highly safe. Furthermore, its cost is low compared to the pharmaceutical agent so that it may be used to improve hygiene in a variety of area.

Example 5

(Bactericidal Test Against Bacteria Live in Gastrointestinal System as a Contaminant of Medical Endoscope)
(1) Test Method
1) Bacteria to be Tested The disinfection effect of the aqueous hypochlorous acid solution was confirmed by using the following bacteria to be tested.

Escherichia coli (Escherichia coli)
Salmonella Enteritidis (Salmonella)
Candida sp. (Candida)
Pseudomonas aeruginosa (Pseudomonas aeruginosa)
2) Preparation of the Test The aqueous hypochlorous acid solution is diluted so as to have the effective chlorine concentration, 200, 20, 5, 2, 1, 0.5 ppm respectively to prepare the test samples. 5 mL portions of these samples are respectively dispensed into 20 mL test tubes. As the reference, the sterilized pure water cot containing the aqueous hypochlorous acid solution is used.
3) Pre-Culture As to both of E. coli and Salmonella, the bacteria to be tested are subjected to standing culture in TSB (Tryptic Soy Broth) at 35° C. for 20 to 24 hours. The bacteria concentrations of the solution to be tested are adjusted by using the sterilized pure water. The bacteria concentration of E. coli was $1.2 \times 10^6$/mL, and Salmonella was $1.7 \times 10^6$/mL.

Candida is cultured in PDA (Potato Dextrose Agar) medium at 25° C. for 44 to 48 hours. Cultured bacteria cells are suspended in the sterilized pure water to prepare the bacterial suspension, wherein the bacterial number was $2.7 \times 10^5$/mL.

*Pseudomonas* is subjected to the standing culture in TSB at 25° C. for 44 to 48 hours. Cultured bacteria cells are suspended in the sterilized pure water to prepare the bacterial suspension, wherein the bacterial number was $2.3 \times 10^6$/mL.

4) Test Methods 0.2 mL portion of the bacteria suspension is inoculated into each sample, and then mixed. At the predetermined time points (0.5 minute. 5 minutes, and 10 minutes), 0.2 mL portion is taken out from each sample, and suspended in 1.8 mL of the sterilized pure water containing 1 mg/mL of sodium thiosulfate to prepare the suspension. Both of 0.1 mL of the suspension and 10× dilution prepared by using the sterilized pure water containing 1 mg/mL of sodium thiosulfate are streaked on SA agar plate for the bacteria or PDA agar plate for the yeasts. As the reference, the sterilized pure water without sodium thiosulfate is used. The plates are incubated, and then, the appeared colony numbers are counted to obtain the viable cell numbers.

5) Determination

The appeared colony numbers at each time point and each concentration are respectively counted to obtain the viable cell numbers, and determined the bactericidal effects.

(2) Test Results

As shown in the following 13 to 16, all of the microbes used in the test are disinfected by treating with the aqueous hypochlorous acid solution of which effective chlorine concentration is 5 ppm for 0.5 minute.

TABLE 13

Disinfection capability to *E. coli* (viable cell number)

| Conc. (ppm) | Treatment time (min.) | | |
|---|---|---|---|
| | 0.5 | 5 | 10 |
| 200 | 0 | 0 | 0 |
| 20 | 0 | 0 | 0 |
| 5 | 0 | 0 | 0 |
| 2 | 340 | 12 | 0 |
| 1 | 350 | 24 | 0 |
| 0.5 | 310 | 21 | 0 |

Control: 490

TABLE 14

Disinfection capability to *Salmonella* (viable cell number)

| Conc. (ppm) | Treatment time (min.) | | |
|---|---|---|---|
| | 0.5 | 5 | 10 |
| 200 | 0 | 0 | 0 |
| 20 | 0 | 0 | 0 |
| 5 | 0 | 0 | 0 |
| 2 | 270 | 3 | 0 |
| 1 | 230 | 12 | 0 |
| 0.5 | 270 | 23 | 0 |

Control: 680

TABLE 15

Disinfection capability to *Candida* (viable cell number)

| Conc. (ppm) | Treatment time (min.) | | |
|---|---|---|---|
| | 0.5 | 5 | 10 |
| 200 | 0 | 0 | 0 |
| 20 | 0 | 0 | 0 |
| 5 | 0 | 0 | 0 |
| 2 | 710 | 3 | 0 |
| 1 | 680 | 63 | 0 |
| 0.5 | 880 | 58 | 0 |

Control: 1,100

TABLE 16

Disinfection capability to *Pseudomonas* (viable cell number)

| Conc. (ppm) | Treatment time (min.) | | |
|---|---|---|---|
| | 0.5 | 5 | 10 |
| 200 | 0 | 0 | 0 |
| 20 | 0 | 0 | 0 |
| 5 | 0 | 0 | 0 |
| 2 | 660 | 0 | 0 |
| 1 | 550 | 0 | 0 |
| 0.5 | 530 | 0 | 0 |

Control: 920

Example 6

(Confirmation of Antiviral Effects)

As the sample to be tested, the aqueous hypochlorous acid solution, which is produced on Jun. 27, 2018 and received on Jun. 28, 2018, was used (product name: Doctor Water (registered trademark)). The effective concentration thereof is adjusted 50 ppm.

As the virus strain, Feline calicivirus (FCV/F9), Mouse norovirus (MNV CW1), Coxsackie virus (CA7) and B5 (CB5), Influenza virus (A/PR8 and A/USSR/92/97), Herpes simplex virus type 1 (HSV-HF) and type 2 (HSV-UW), Adeno virus type 3 (Ad.3) and type 5 (Ad.5) as well as type 8 (Ad.8) were used.

As the sensitive cell CRFK cell for Feline calicivirus, RAW264.7 cell for Mouse norovirus, Vero cell both for Coxsackie virus and Herpes simplex virus, MCK cell for Influenza virus, A549 cell for Adenovirus, are used.

Antiviral test methods are as follows. Firstly, 100 μL portion of stock viral solution is added to 900 μL sample solution, and then mixed.

After mixing, at the time point, 10 second, 1 minute, 5 minutes, 10 minutes (from finishing each treatment), 10× serial dilutions thereof are prepared by using the medium containing 0.1 N sodium thiosulfate. 10 μL portions are taken from the serial dilutions, they are contacted with the sensitive cells; and then, 100 μL of maintaining medium is added to them respectively, and incubated at 37° C. for 3 to 10 days in a 5% $CO_2$ incubator.

Both morphological change of the cell and CPE (cytopathic effect), which are caused by infection of the viruses to the sensitive cells, are observed macroscopically under an optical microscope to confirm the cytopathic effect at which dilution rate, and to obtain $TCID_{50}$ (50% tissue culture infectious dose). Results are shown in the following Table 17.

TABLE 17

| Virus strain name | Treatment time | | |
|---|---|---|---|
| | 0 sec. | 10 sec. | 1 min. |
| | Viable cell number | | |
| Feline calicivirus FCV/F9 | $10^{5.64}$ | $10^{1.8}$ | $<10^{0.5}$ |
| Mouse norovirus MNV CW1 | $10^{5.0}$ | $10^{1.5}$ | $10^{0.75}$ |
| Coxsackie virus CA7 | $10^{5.18}$ | $10^{3.0}$ | $10^{2.7}$ |
| Coxsackie virus CB5 | $10^{5.65}$ | $10^{5.59}$ | $10^{5.0}$ |
| Influenza 8 virus A/PR8 | $10^{4.20}$ | $<10^{0.5}$ | $<10^{0.5}$ |
| Influenza 8 virus A/USSR/92/97 | $10^{3.5}$ | $<10^{0.5}$ | $<10^{0.5}$ |
| Herpes simplex virus HSV-HF | $10^{3.46}$ | $<10^{0.5}$ | $<10^{0.5}$ |
| Herpes simplex virus HSV-UW | $10^{4.17}$ | $<10^{0.5}$ | $<10^{0.5}$ |
| Adenovirus Ad.3 | $10^{4.09}$ | $<10^{0.5}$ | $<10^{0.5}$ |

As shown in table 7, the aqueous hypochlorous acid solution of the present invention showed high antiviral effects to any viruses tested.

Example 7

(Measurement of the Effects when pH of the Aqueous Hypochlorous Acid Solution is Chanted)

(1) The Samples to be Tested

The original solution having the effective chlorine concentration in the range between 150 to 260 ppm are adjusted pH 3.0 to 6.5 by using dilute HCl to prepare the sample to be tested. The effective chlorine concentration is measured by using the Handy Water Meter, Model AQ-101 (Shibata Scientific Technology Ltd.). The measurement time are set to 10 second, 1 minute, 5 minutes and 10 minutes.

(2) Test Method (2-1) The Bacteria to be Tested

In the tests, 2 bacteria shown in the following Tables 18 and 19 and either of the agar plate or liquid medium are used.

(2-2) Pre-Culture

The bacteria to be tested are re-cultured under the following conditions and then subjected to the test. The pre-culture of the bacteria is conducted by inoculating either of *Clostridium butyricum* NBRC13949 strain (*Clostridium butyricum* NBRC13949) or *Clostridium sporogenes* strain (*Clostridium sporogenes* IFO13950) in 10 mL of CS liquid medium being composed of 2.0% corn starch, 2.0% amino acid solution and 0.75% calcium carbonate; and then they are incubated at 37° C. for 24 hours as anaerobic culture by using carbonate gas replacement steel wool method.

(2-3) Preparation of the Bacteria Suspension

The pre-cultured bacteria to be tested as described above is adjusted so as to be $1\times10^7$ to $1\times10^6$ CFU/mL by using the sterilized saline.

(2-4) Test Method

The effects of the aqueous hypochlorous acid solution against the bacteria to be tested shown in Tables 17 and 18 were studied by using brain heart infusion agar plates.

100 μL portion of the bacteria suspension is added into the test solution 900 μL prepared as described above, and then mixed. At each time point, 10 seconds, 1 minute, 5 minutes, and 10 minutes later from the mixing, 10× serial dilutions are prepared by using BHI medium supplemented with 0.1 N sodium thiosulfate, and then 10 μL portions are taken out from the samples respectively and streaked on BHI agar plate. The plates are subjected to the anaerobic culture by using carbonate gas replaced steel wool method at 37° C. for 24 hours, and then the bacterial number is counted.

(2-5) Decision Method and the Results

By concentrations, the appeared colonies at each treatment time is counted to obtain the viable cell number to decide the bactericidal effects. Results are shown in Tables 18 and 19.

TABLE 18

Viable bacteria number at each treatment time (Dilution rate = 1)

| *Clostridium butyricum* NBRC13949 | | | | Treatment time (sec.) 0 Starting Microbe No. | 10 | 60 | 300 | 600 | Decision (sec.)* |
|---|---|---|---|---|---|---|---|---|---|
| | | | | | Viable bacteria No. | | | | |
| Effective | 150 | pH | 3.0 | $1.0\times10^6$ | $<\times10^2$ | $<\times10^2$ | $<\times10^2$ | $<\times10^2$ | <10 |
| chlorine | | | 4.5 | | $<\times10^2$ | $<\times10^2$ | $<\times10^2$ | $<\times10^2$ | <10 |
| conc. | | | 5.5 | | $<\times10^2$ | $<\times10^2$ | $<\times10^2$ | $<\times10^2$ | <10 |
| (ppm) | | | 6.5 | | $<\times10^2$ | $<\times10^2$ | $<\times10^2$ | $<\times10^2$ | <10 |
| | 200 | pH | 3.0 | $1.0\times10^6$ | $<\times10^2$ | $<\times10^2$ | $<\times10^2$ | $<\times10^2$ | <10 |
| | | | 4.5 | | $<\times10^2$ | $<\times10^2$ | $<\times10^2$ | $<\times10^2$ | <10 |
| | | | 5.5 | | $<\times10^2$ | $<\times10^2$ | $<\times10^2$ | $<\times10^2$ | <10 |
| | | | 6.5 | | $<\times10^2$ | $<\times10^2$ | $<\times10^2$ | $<\times10^2$ | <10 |
| | 260 | pH | 3.0 | $1.0\times10^6$ | $<\times10^2$ | $<\times10^2$ | $<\times10^2$ | $<\times10^2$ | <10 |
| | | | 4.5 | | $<\times10^2$ | $<\times10^2$ | $<\times10^2$ | $<\times10^2$ | <10 |
| | | | 5.5 | | $<\times10^2$ | $<\times10^2$ | $<\times10^2$ | $<\times10^2$ | <10 |
| | | | 6.5 | | $<\times10^2$ | $<\times10^2$ | $<\times10^2$ | $<\times10^2$ | <10 |

*Disinfection time
Unit: CFU/mL

TABLE 19

Viable bacteria number at each treatment time (Dilution rate = 1)

| Clostridium sporogenes IFO13950 | | | 0 Starting Microbe No. | Treatment time (sec.) | | | | Decision (sec.)* |
|---|---|---|---|---|---|---|---|---|
| | | | | 10 | 60 | 300 | 600 | |
| | | | | Viable bacteria No. | | | | |
| Effective chlorine conc. (ppm) | 150 | pH 3.0 | $1.0 \times 10^7$ | $<\times 10^2$ | $<\times 10^2$ | $<\times 10^2$ | $<\times 10^2$ | <10 |
| | | 4.5 | | $<\times 10^2$ | $<\times 10^2$ | $<\times 10^2$ | $<\times 10^2$ | <10 |
| | | 5.5 | | $<\times 10^2$ | $<\times 10^2$ | $<\times 10^2$ | $<\times 10^2$ | <10 |
| | | 6.5 | | $<\times 10^2$ | $<\times 10^2$ | $<\times 10^2$ | $<\times 10^2$ | <10 |
| | 200 | pH 3.0 | $1.0 \times 10^7$ | $<\times 10^2$ | $<\times 10^2$ | $<\times 10^2$ | $<\times 10^2$ | <10 |
| | | 4.5 | | $<\times 10^2$ | $<\times 10^2$ | $<\times 10^2$ | $<\times 10^2$ | <10 |
| | | 5.5 | | $<\times 10^2$ | $<\times 10^2$ | $<\times 10^2$ | $<\times 10^2$ | <10 |
| | | 6.5 | | $<\times 10^2$ | $<\times 10^2$ | $<\times 10^2$ | $<\times 10^2$ | <10 |
| | 260 | pH 3.0 | $1.0 \times 10^7$ | $<\times 10^2$ | $<\times 10^2$ | $<\times 10^2$ | $<\times 10^2$ | <10 |
| | | 4.5 | | $<\times 10^2$ | $<\times 10^2$ | $<\times 10^2$ | $<\times 10^2$ | <10 |
| | | 5.5 | | $<\times 10^2$ | $<\times 10^2$ | $<\times 10^2$ | $<\times 10^2$ | <10 |
| | | 6.5 | | $<\times 10^2$ | $<\times 10^2$ | $<\times 10^2$ | $<\times 10^2$ | <10 |

*Disinfection time
Unit: CFU/mL

At any concentration or pH, the disinfection time of 2 *Clostridium* strains described above is less than 10 seconds. Therefore, the sample has effects to disinfect *Clostridium* by using the aqueous hypochlorous acid solution having any chlorine concentration or pH in very short time.

Example 8

(Measurement of the Disinfection Effects Against the Bacteria)
(1) The Sample to be Tested
As subject samples, the aqueous hypochlorous acid solution prepared in Example 7 (1) is used. The subject sample is used to prepare the following samples to be used the decision of the bactericidal effects against the following bacteria.
(2) Test Method
1) The Bacteria to be Tested
*Clostridium* shown in the following Tables 20 and 21, *Clostridium butyricum* (*Clostridium butyricum* NBRC13949) and *Clostridium sporogenes* (*Clostridium sporogenes* IFO 13950) were used.
2) Pre-Culture
The bacteria to be tested are subjected standing culture by using CDC Anaerobe blood agar (BD Japan Inc., hereinbelow, it is sometimes referred to as "blood agar") as the medium at 37° C. for 24 to 48 hours in the anaerobic chamber (pre-culture), and then subjected to the test. The bacterial numbers used are adjusted from $1 \times 10^7$ to $1 \times 10^8$ CFU/mL.
3) Test Method
0.1 mL portions of respective solutions containing the bacteria (hereinbelow, it is referred to as a "bacteria suspension") is inoculated into 0.9 mL of the sample having respective concentrations 0.9 mL, and then mixed to prepare the sample to be tested. At predetermined time (10 second, 1 minute, 5 minutes, and 10 minutes) after the inoculation, 20 μL portions are taken out from each sample, and then they are inoculated into 180 μL of the maintaining medium for the bacteria to prepare 10× serial dilutions.
From the 10× serial dilutions of the bacteria, 10 μL portions are respectively taken out, and then spread on the blood agar plate by using a bacteria spreader. The blood agar plates on which each sample is spread are cultured at 37° C. for 24 hours in the anaerobic chamber. After that, the appeared colonies on the plates are counted.
(3) Test Results
The results of the bactericidal tests at each time points are shown in Tables 20 and 21, dividing bacteria.

TABLE 20

| *Clostridium butyricum* | | Ref. section | | Sample section (ppm) | | |
|---|---|---|---|---|---|---|
| pH of sample | Treatment time | Negative Viable cell numbers | Positive | 150 | 200 | 260 |
| | | | | Viable cell numbers | | |
| 3.0 | 10 sec. | <100 | $7.4 \times 10^5$ | <100 | <100 | <100 |
| | 60 sec. | <100 | $7.4 \times 10^5$ | <100 | <100 | <100 |
| 4.5 | 10 sec. | <100 | $7.4 \times 10^5$ | <100 | <100 | <100 |
| | 60 sec. | <100 | $7.4 \times 10^5$ | <100 | <100 | <100 |
| 5.5 | 10 sec. | <100 | $7.4 \times 10^5$ | <100 | <100 | <100 |
| | 60 sec. | <100 | $7.4 \times 10^5$ | <100 | <100 | <100 |
| 6.5 | 10 sec. | <100 | $7.4 \times 10^5$ | <100 | <100 | <100 |
| | 60 sec. | <100 | $7.4 \times 10^5$ | <100 | <100 | <100 |

[TCID$_{50}$/50 μL]

TABLE 21

| *Clostridium sporogenes* | | Ref. section | | Sample section (ppm) | | |
|---|---|---|---|---|---|---|
| pH of sample | Treatment time | Negative Viable cell numbers | Positive | 150 | 200 | 260 |
| | | | | Viable cell numbers | | |
| 3.0 | 10 sec. | <100 | $3.4 \times 10^7$ | <100 | <100 | <100 |
| | 60 sec. | <100 | $3.4 \times 10^7$ | <100 | <100 | <100 |
| 4.5 | 10 sec. | <100 | $3.4 \times 10^7$ | <100 | <100 | <100 |
| | 60 sec. | <100 | $3.4 \times 10^7$ | <100 | <100 | <100 |
| 5.5 | 10 sec. | <100 | $3.4 \times 10^7$ | <100 | <100 | <100 |
| | 60 sec. | <100 | $3.4 \times 10^7$ | <100 | <100 | <100 |
| 6.5 | 10 sec. | <100 | $3.4 \times 10^7$ | <100 | <100 | <100 |
| | 60 sec. | <100 | $3.4 \times 10^7$ | <100 | <100 | <100 |

[TCID$_{50}$/50 μL]

From the results of the bactericidal effects by using each *Clostridium* shown in Tables 20 & 21, it was decided that the colony appearance was not observed when they are treated with the solution containing the effective chlorine concentration not less than 150 ppm within 10 seconds so that they died out. Accordingly, it was shown that the aqueous hypochlorous acid of the present invention has high bactericidal effects against the anaerobe, *Clostridium*, in low pH range.

Example 9

(Virucidal Effects Against Viruses)
(1) Strains to be Tested

Feline panleukopenia virus (ATCC (Registered trademark) VR-648) and Canine parvovirus (ATCC VR-2017), both of which are parvovirus belonging to Parvoviridae, and Measles virus (ATCC VR-24) belonging to Paramyxoviridae were used.

As the sensitive cells, CRFK cells (JCRB9035) for the growth of Feline panleukopenia virus, A-72 cells (ATCC CRL-1542) for that of Canine parvovirus, and Vero cells (former DS Pharma Co. Ltd., present KAC Co. Ltd.) for that of Measles virus were used to prepare the virus suspensions respectively. The references and sample suspensions used for the decision of the effects of the viruses are shown in the following table 22.

TABLE 22

| | Virus name | | |
|---|---|---|---|
| | Feline panleukopenia virus | Canine parvovirus | Measles |
| Negative control | Phosphate buffer | Phosphate buffer | Phosphate buffer |
| Positive control (×10 dilution) | Virus suspension | Virus suspension | Virus suspension |
| Sample (×10 dilution) | the aqueous hypochlorous acid solution | the aqueous hypochlorous acid solution | the aqueous hypochlorous acid solution |

(2) Preparation of the Subject to be Tested

The effective chlorine concentrations of the aqueous hypochlorous acid solution shown in Table 22 are respectively adjusted to 150 ppm, 200 ppm, and 260 ppm, as well as pH thereof is set to 3.0, 4.5, 5.5, and 6.5 to prepare the subject to be tested (see the following Tables 4 to 6). The effective chlorine concentrations are determined by using High concentration Effective Chlorine Meter RC-2Z (Kasahara Chemical Instruments Corp.). pH was measured by using Personal pH Meter MODEL PH82 (Yokogawa Electric Corporation). The following samples were prepared by using the subject to be tested, and then their antiviral effects are determined. Note that gas generation from the aqueous hypochlorous acid solution was not observed, it confirms that the aqueous hypochlorous acid solution does not generate chlorine gas even in low pH range such as pH 3.0 to 5.5.

Liquid volume both of the references and samples are 1,000 µL. The negative control is phosphate buffer, the positive control contains the virus suspension 100 µL+phosphate buffer 900 µL, the sample to be tested contains the virus suspension 100 µL+the sample to be tested 900 µL (the aqueous hypochlorous acid solution).

(3) Determination Method

The determination for the virus titer was conducted by the steps of diluting the sample 10 times as described above, inoculating them to respective sensitive cells. The virus titer was decided with the microscope, both of the morphological change of the sensitive cells caused by the virus infection and CPE (cytopathic effect) are macroscopically observed at the dilution rate.

Virus titration is measured according to the following procedure.

100 µL of the virus suspension is added into 900 µL of the sample to mix by using Vortex mixer for 10 seconds or 60 seconds to prepare the sample (the mixture of the virus suspension and the aqueous hypochlorous acid solution). The mixture is diluted with the maintaining medium for the cells as mentioned above to prepare 10× serial dilutions.

In the case of Measles virus, 10 µL portions of the prepared serial dilutions are inoculated into the predetermined wells of 96 well plate, wherein the sensitive cells are pre-cultured. In the case both of Feline panleukopenia virus and Canine parvovirus, 50 µL portions of the prepared serial dilutions are predetermined wells of 24 well plate, wherein the sensitive cells are pre-cultured.

After the inoculation of each virus to the predetermined wells in the plate, each plate is cultured at 37° C. for 7 to 10 days in $CO_2$ incubator. The cytopathic effect is observed with the microscope to obtain $TCID_{50}$ by using Behrens-Karber. Results are shown in the following Tables 23 to 25.

TABLE 23

| Feline panleukopenia virus | | Ref. section | | Test Section (ppm) | | |
|---|---|---|---|---|---|---|
| pH of sample | Treatment time | Negative Viable cell number | Positive | 150 | 200 | 260 |
| | | | | Viable cell number | | |
| 3.0 | 10 sec. | $<10^{0.5}$ | $10^{2.9}$ | $<10^{0.5}$ | $<10^{0.5}$ | $<10^{0.5}$ |
| | 60 sec. | $<10^{0.5}$ | $10^{2.9}$ | $<10^{0.5}$ | $<10^{0.5}$ | $<10^{0.5}$ |
| 4.5 | 10 sec. | $<10^{0.5}$ | $10^{2.9}$ | $<10^{0.5}$ | $<10^{0.5}$ | $<10^{0.5}$ |
| | 60 sec. | $<10^{0.5}$ | $10^{2.9}$ | $<10^{0.5}$ | $<10^{0.5}$ | $<10^{0.5}$ |
| 5.5 | 10 sec. | $<10^{0.5}$ | $10^{2.9}$ | $<10^{0.5}$ | $<10^{0.5}$ | $<10^{0.5}$ |
| | 60 sec. | $<10^{0.5}$ | $10^{2.9}$ | $<10^{0.5}$ | $<10^{0.5}$ | $<10^{0.5}$ |
| 6.5 | 10 sec. | $<10^{0.5}$ | $10^{2.9}$ | $<10^{0.5}$ | $<10^{0.5}$ | $<10^{0.5}$ |
| | 60 sec. | $<10^{0.5}$ | $10^{2.9}$ | $<10^{0.5}$ | $<10^{0.5}$ | $<10^{0.5}$ |

[$CID_{50}$/50 µL]

TABLE 24

| Canine parvovirus | | Ref. section | | Test Section (ppm) | | |
|---|---|---|---|---|---|---|
| pH of sample | Treatment time | Negative Viable cell number | Positive | 150 | 200 | 260 |
| | | | | Viable cell number | | |
| 3.0 | 10 sec. | $<10^{0.5}$ | $10^{2.7}$ | $<10^{0.5}$ | $<10^{0.5}$ | $<10^{0.5}$ |
| | 60 sec. | $<10^{0.5}$ | $10^{2.7}$ | $<10^{0.5}$ | $<10^{0.5}$ | $<10^{0.5}$ |
| 4.5 | 10 sec. | $<10^{0.5}$ | $10^{2.7}$ | $<10^{0.5}$ | $<10^{0.5}$ | $<10^{0.5}$ |
| | 60 sec. | $<10^{0.5}$ | $10^{2.7}$ | $<10^{0.5}$ | $<10^{0.5}$ | $<10^{0.5}$ |
| 5.5 | 10 sec. | $<10^{0.5}$ | $10^{2.7}$ | $<10^{0.5}$ | $<10^{0.5}$ | $<10^{0.5}$ |
| | 60 sec. | $<10^{0.5}$ | $10^{2.7}$ | $<10^{0.5}$ | $<10^{0.5}$ | $<10^{0.5}$ |
| 6.5 | 10 sec. | $<10^{0.5}$ | $10^{2.7}$ | $<10^{0.5}$ | $<10^{0.5}$ | $<10^{0.5}$ |
| | 60 sec. | $<10^{0.5}$ | $10^{2.7}$ | $<10^{0.5}$ | $<10^{0.5}$ | $<10^{0.5}$ |

[$TCID_{50}$/50 µL]

TABLE 25

| Measle virus | | Ref. section | | Test Section (ppm) | | |
|---|---|---|---|---|---|---|
| pH of sample | Treatment time | Negative Viable cell number | Positive Viable cell number | 150 | 200 | 260 |
| 3.0 | 10 sec. | $<10^{0.5}$ | $10^{3.5}$ | $<10^{0.5}$ | $<10^{0.5}$ | $<10^{0.5}$ |
|  | 60 sec. | $<10^{0.5}$ | $10^{3.5}$ | $<10^{0.5}$ | $<10^{0.5}$ | $<10^{0.5}$ |
| 4.5 | 10 sec. | $<10^{0.5}$ | $10^{3.5}$ | $<10^{0.5}$ | $<10^{0.5}$ | $<10^{0.5}$ |
|  | 60 sec. | $<10^{0.5}$ | $10^{3.5}$ | $<10^{0.5}$ | $<10^{0.5}$ | $<10^{0.5}$ |
| 5.5 | 10 sec. | $<10^{0.5}$ | $10^{3.5}$ | $<10^{0.5}$ | $<10^{0.5}$ | $<10^{0.5}$ |
|  | 60 sec. | $<10^{0.5}$ | $10^{3.5}$ | $<10^{0.5}$ | $<10^{0.5}$ | $<10^{0.5}$ |
| 6.5 | 10 sec. | $<10^{0.5}$ | $10^{3.5}$ | $<10^{0.5}$ | $<10^{0.5}$ | $<10^{0.5}$ |
|  | 60 sec. | $<10^{0.5}$ | $10^{3.5}$ | $<10^{0.5}$ | $<10^{0.5}$ | $<10^{0.5}$ |

[$TCID_{50}$/50 µL]

As shown in Tables 23 to 25, in positive control section, multiplication of the viruses is observed in all of them. However, it was not observed in test section. Accordingly, the aqueous hypochlorous acid solution of the present invention is virucidal effects against Feline panleukopenia virus, Canine parvovirus, and Measles viruses in low pH range.

INDUSTRIAL APPLICABILITY

The present invention is antimicrobe agent in wide range of fields for disinfecting both of hands and fingers, together with cleaning of kitchen ware so that it is particularly available in medical and pharmaceutical area.

The invention claimed is:

1. An antimicrobial agent consisting a hypochlorous acid aqueous solution preventing chlorine gas generation under pH 7, wherein said aqueous solution consists of sodium hypochlorite, purified water, and 9.5-10.5% (W/V) dilute hydrochloric acid,
and the effective chlorine concentration range in said aqueous solution is between 150 and 260 ppm, and pH range of said aqueous solution is between 3.0 and 4.5, whereby
said antimicrobial agent disinfects bacteria within 1 minute.

2. The antimicrobial agent according to claim 1, wherein the bacterium is any one of bacterium selected from the group consisting of *Clostridium butyricum* and *Clostridium sporogenes*.

3. The antimicrobial agent according to claim 2, wherein said hypochlorous acid aqueous solution consists of sodium hypochlorite as a food additive, purified water as defined by the Japanese Pharmacopoeia, and dilute hypochlorous acid solution as defined in the Japanese Pharmacopoeia.

4. A method for disinfecting a microbe comprising a step; immersing a microbe in the antimicrobial agent according to claim 2 for a period from 0.5 minutes to 10 minutes.

5. The antimicrobial agent according to claim 1, wherein said hypochlorous acid aqueous solution consists of sodium hypochlorite as a food additive, purified water as defined by the Japanese Pharmacopoeia, and dilute hypochlorous acid solution as defined in the Japanese Pharmacopoeia.

6. A method for disinfecting a microbe comprising a step; immersing a microbe in the antimicrobial agent according to claim 1 for a period from 0.5 minutes to 10 minutes.

7. An antimicrobial agent consisting a hypochlorous acid aqueous solution preventing chlorine gas generation under pH 7, wherein said aqueous solution consists of sodium hypochlorite, purified water, and 9.5-10.5% (W/V) dilute hydrochloric acid and the effective chlorine concentration range in said aqueous solution is from 50 to 260 ppm, and pH range of said aqueous solution is between 3.0 and 6.7, for inhibiting the growth of any one of microbe selected from the group consisting of a yeast, a fungus, and a virus.

8. The antimicrobial agent according to claim 7, wherein the effective chlorine concentration range in said aqueous solution is from 50 to 210 ppm, and pH range of said aqueous solution is between 6.3 and 6.7, for inhibiting the growth of any one of microbe selected from the group consisting of a yeast, a fungus, and a virus.

9. A method for disinfecting a microbe comprising a step; immersing any one of microbe selected from the group consisting of the yeast, the fungus, and the virus in the antimicrobial agent according to claim 8 for a period from 0.5 minutes to 10 minutes.

10. The antimicrobial agent according to claim 7, wherein the yeast is any one of yeast belonging *Rhodotorula* sp.

11. A method for disinfecting a microbe comprising a step;
immersing any one of microbe selected from the group consisting of the yeast, the fungus, and the virus in the antimicrobial agent according to claim 10 for a period from 0.5 minutes to 10 minutes.

12. The antimicrobial agent according to claim 7, wherein the fungus is any one of fungus selected from the group consisting of *Cladosporium cladosporioides, Penicillium roqueforti, Penicillium glabrum, Aspergillus niger, Eurotium amstelodami, Neosartorya fischeri, Emericella nidulans, Fusarium,* and *Alternaria*.

13. The antimicrobial agent according to claim 7, wherein the virus is Norovirus.

14. A method for disinfecting a microbe comprising a step;
immersing any one of microbe selected from the group consisting of the yeast, the fungus, and the virus in the antimicrobial agent according to claim 7 for a period from 0.5 minutes to 10 minutes.

15. The antimicrobial agent according to claim 7, wherein said hypochlorous acid aqueous solution consists of sodium hypochlorite as a food additive, purified water as defined by the Japanese Pharmacopoeia, and dilute hypochlorous acid solution as defined in the Japanese Pharmacopoeia.

16. A method for producing the antimicrobial agent according to claim 7, wherein the method comprises steps of; (a) dissolving sodium hypochlorite into purified water to prepare sodium hypochlorite solution; and (b) adjusting pH of the hypochlorous solution between pH 3.0 and 6.7 by adding 9.5-10.5 w/v % dilute hydrochloric acid solution.

17. An antimicrobial agent including consisting a hypochlorous acid aqueous solution preventing chlorine gas generation under pH 7, wherein said aqueous solution consists—of sodium hypochlorite, purified water, and 9.5-10.5% (W/V) dilute hydrochloric acid,
and the effective chlorine concentration range in said aqueous solution is between 150 and 260 ppm, and pH range of said aqueous solution is between 3.0 and 6.5, whereby
said antimicrobial agent disinfects a virus within 10 seconds.

18. The antimicrobial agent according to claim 17, wherein
the virus is any one of virus selected from the group consisting of Canine parvovirus, Feline panleukopenia virus, and Measles virus.

19. A method for disinfecting a microbe comprising a step;
immersing the virus in the antimicrobial agent according to claim 17 for a period from 10 seconds to 60 seconds.

* * * * *